(12) United States Patent
Hinckley

(10) Patent No.: US 7,817,498 B1
(45) Date of Patent: Oct. 19, 2010

(54) MEDICAL APPARATUS HAVING ELAPSED TIME INDICATED AND METHOD OF USE

(75) Inventor: C. Martin Hinckley, Perry, UT (US)

(73) Assignee: Michael R. Schramm, South Perry, UT (US)

(*) Notice: Subject to any disclaimer, the term of this patent is extended or adjusted under 35 U.S.C. 154(b) by 179 days.

(21) Appl. No.: 11/747,883

(22) Filed: May 11, 2007

(51) Int. Cl.
G04B 47/00 (2006.01)
G04F 1/00 (2006.01)
A61M 5/00 (2006.01)
A61M 3/00 (2006.01)

(52) U.S. Cl. .................. 368/10; 368/327; 604/187; 604/189; 604/192

(58) Field of Classification Search ............ 368/10, 368/110–113, 327; 600/97.03, 100.03; 604/97.03, 604/100.03, 187, 189, 192
See application file for complete search history.

(56) References Cited

U.S. PATENT DOCUMENTS

| | | | |
|---|---|---|---|
| 4,903,254 A | 2/1990 | Haas | 368/327 |
| 5,021,046 A * | 6/1991 | Wallace | 604/97.03 |
| 5,058,088 A | 10/1991 | Haas et al. | 368/327 |
| 5,259,838 A * | 11/1993 | Taylor et al. | 604/97.03 |
| 5,364,132 A | 11/1994 | Haas et al. | 283/67 |
| 5,446,705 A | 8/1995 | Haas et al. | 368/327 |
| 5,449,345 A * | 9/1995 | Taylor et al. | 604/100.03 |
| 5,593,390 A * | 1/1997 | Castellano et al. | 604/187 |
| 5,602,804 A | 2/1997 | Haas | 368/327 |
| 5,633,835 A | 5/1997 | Haas | 368/327 |
| 5,665,065 A * | 9/1997 | Colman et al. | 604/66 |
| 5,699,326 A | 12/1997 | Haas et al. | 368/327 |
| 5,715,215 A | 2/1998 | Haas et al. | 368/327 |
| 5,719,828 A | 2/1998 | Haas et al. | 368/327 |
| 5,749,853 A * | 5/1998 | O'Donnell et al. | 604/97.03 |
| 5,785,354 A | 7/1998 | Haas | 283/74 |
| 5,820,602 A * | 10/1998 | Kovelman et al. | 604/187 |
| 5,822,280 A | 10/1998 | Haas | 368/327 |
| 5,862,101 A | 1/1999 | Haas et al. | 368/327 |

(Continued)

FOREIGN PATENT DOCUMENTS

WO WO 03/007088 1/2003

OTHER PUBLICATIONS

Timestrip Limited, Timestrip Smart Labels, Unknown, One page internet advertisement.

*Primary Examiner*—Vit W Miska
(74) *Attorney, Agent, or Firm*—Michael R. Schramm

(57) ABSTRACT

The time measuring and indication device is an invention that automatically measures and indicates elapsed time and is adapted to be connected to an IV or like medical apparatus. The device measures time by means of measuring the flow of a fluid having a known fluid flow rate. Prior to actuation, the device displays a first indicia such as the word "GOOD", and after actuation and a predetermined lapse of time, the device displays a second indicia such as the word "EXPIRED". The device further includes a means to halt or stop the time measuring function and to permanently display the elapsed period of time once the time measuring function is stopped. The time measuring and indication device further includes a means to prevent use of an apparatus such as an IV or like medical apparatus to which the device is attached, without activating the time measuring function of the device.

28 Claims, 11 Drawing Sheets

U.S. PATENT DOCUMENTS

| | | |
|---|---|---|
| 5,873,606 A | 2/1999 | Haas et al. .................... 283/75 |
| 5,876,380 A * | 3/1999 | Manganini et al. .......... 604/191 |
| 5,930,206 A | 7/1999 | Haas et al. .................. 368/327 |
| 5,947,369 A | 9/1999 | Frommer et al. ............ 233/382 |
| 5,957,458 A | 9/1999 | Haas et al. .................. 273/269 |
| 6,192,891 B1 * | 2/2001 | Gravel et al. ................ 604/187 |
| 6,277,099 B1 * | 8/2001 | Strowe et al. ............... 604/207 |
| 6,295,252 B1 | 9/2001 | Holt et al. ................... 368/327 |
| 6,452,873 B1 | 9/2002 | Holt et al. ................... 368/327 |
| 6,752,430 B2 | 6/2004 | Holt et al. ..................... 283/72 |
| 6,796,065 B2 | 9/2004 | Haas ....................... 40/661.04 |
| 6,909,671 B2 * | 6/2005 | Setler ......................... 368/113 |
| 6,916,130 B1 | 7/2005 | Holt et al. .............. 400/120.01 |
| 6,932,242 B2 * | 8/2005 | Gerlach et al. .............. 222/113 |
| 7,115,113 B2 * | 10/2006 | Evans et al. ................. 604/189 |
| 7,139,226 B2 | 11/2006 | Haas et al. .................. 368/327 |
| 2002/0107504 A1 * | 8/2002 | Gordon ....................... 604/507 |
| 2004/0015137 A1 * | 1/2004 | Hohlfelder et al. .......... 604/246 |
| 2004/0051368 A1 * | 3/2004 | Caputo et al. ................. 299/1.9 |
| 2004/0054319 A1 * | 3/2004 | Langley et al. ................ 604/67 |
| 2004/0240324 A1 | 12/2004 | Isbitsky et al. .............. 368/327 |
| 2005/0226101 A1 | 10/2005 | Haas et al. .................. 368/327 |
| 2007/0123829 A1 * | 5/2007 | Atterbury et al. ........... 604/207 |
| 2007/0250010 A1 * | 10/2007 | Hohlfelder et al. .......... 604/154 |

* cited by examiner

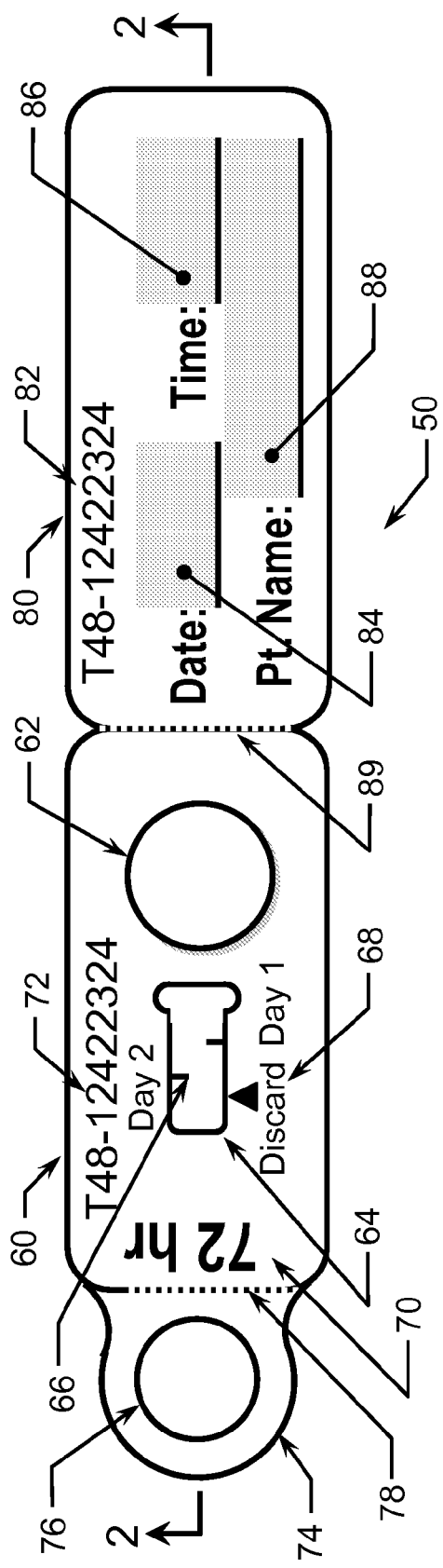
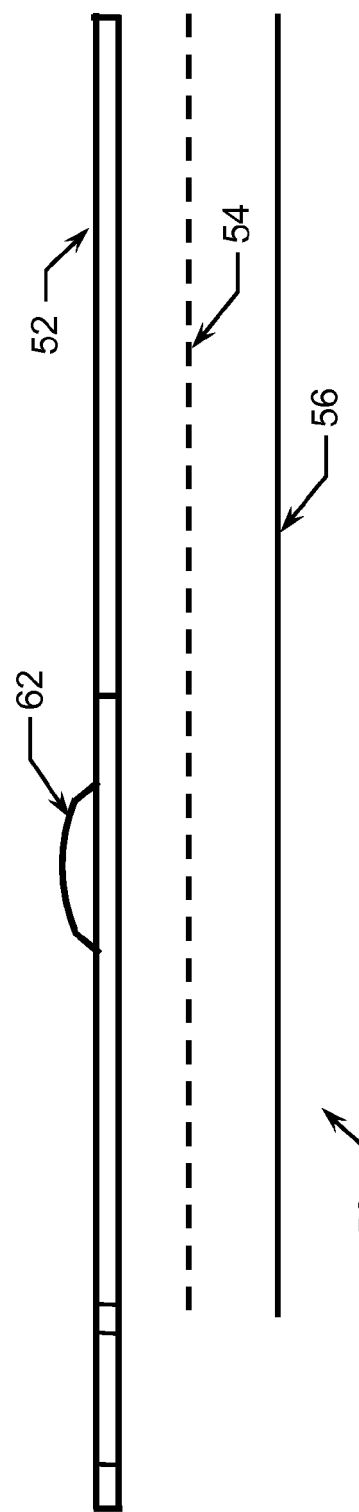
Figure 1
Figure 2

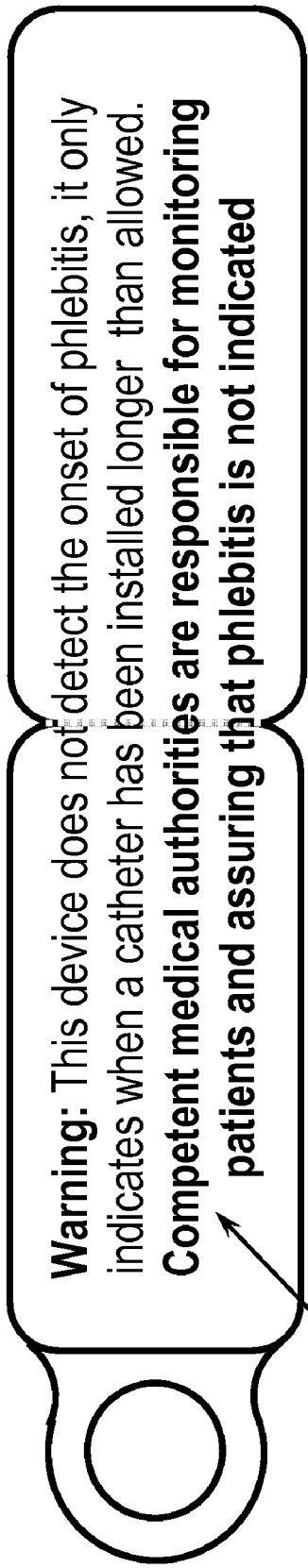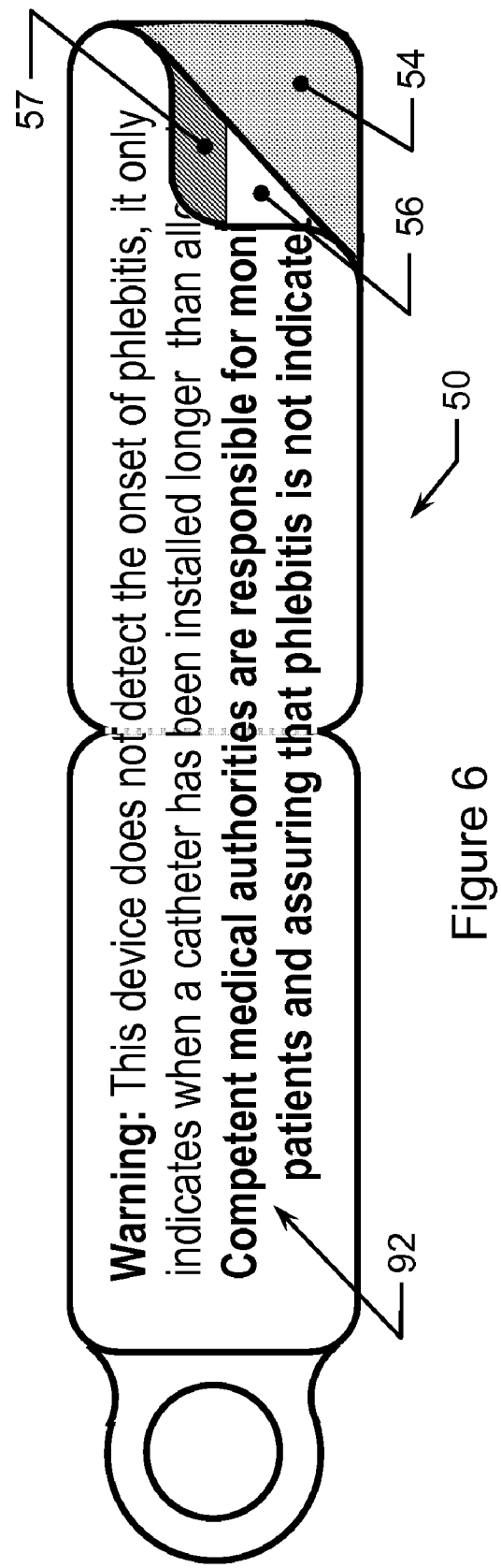

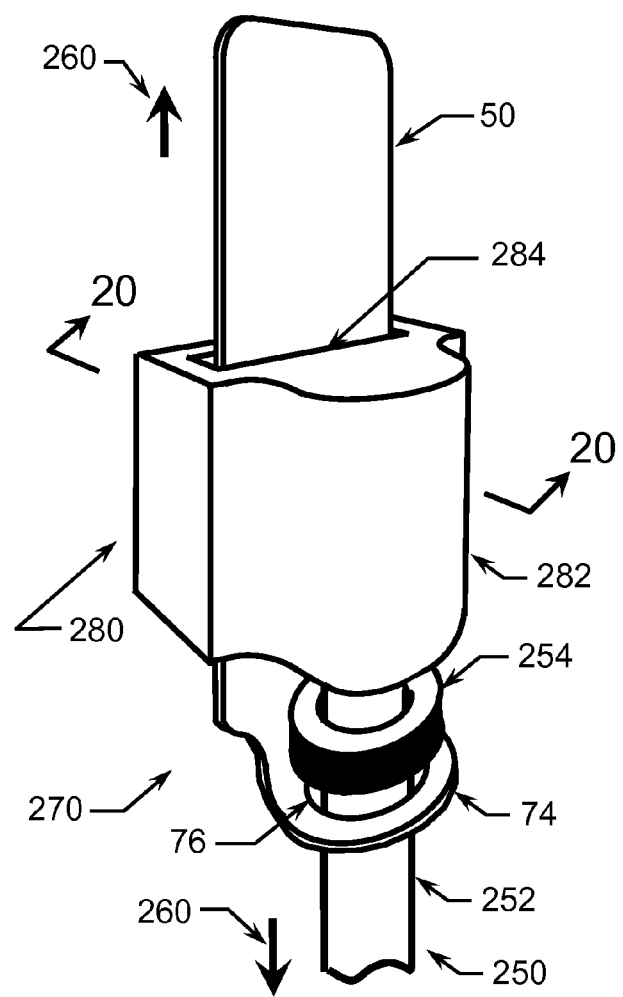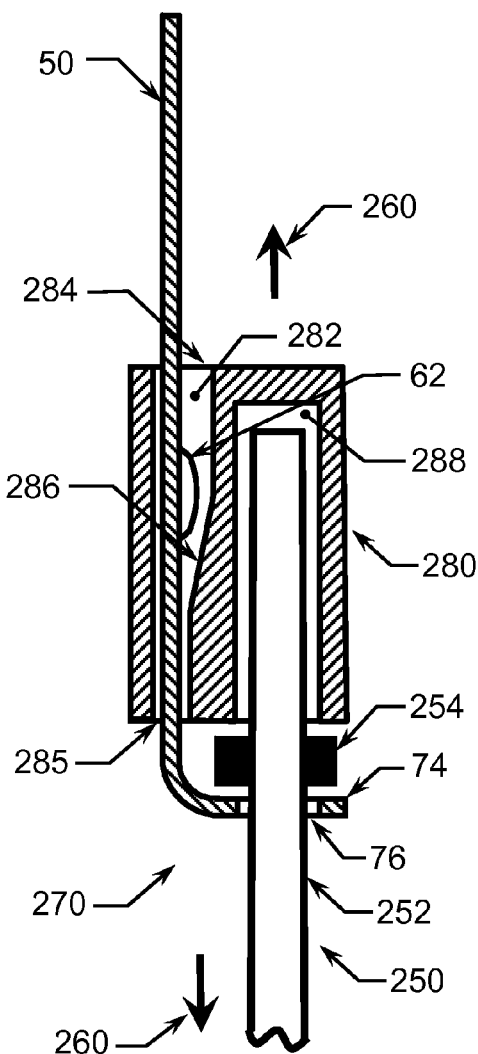
Figure 19
Figure 20

MEDICAL APPARATUS HAVING ELAPSED TIME INDICATED AND METHOD OF USE

BACKGROUND OF THE INVENTION

1. Field of the Invention

This invention relates to devices used to measure and indicate the elapsed time of usage of a medical device and more especially to devices that prevent the usage of a medical device without the initiation of time measurement and to devices that record and indicate elapsed time at the completion of use of a medical device.

2. Description of the Related Art

Many products including common packaged food items and medical products have a finite shelf life defining a time period beyond which such products are rendered ineffective, and may even cause illness or injury. Thus, a need to track or measure the elapsed time from first use to expiration of such products has been identified. In response to such need, various elapsed time indication devices have been developed. An example of such time measuring and indication device is the device disclosed in published U.S. patent application 20040240324 by Ibitsky et al. Ibitsky teaches a device that measures time by means of measuring the migration of a fluid of a known viscosity from a first chamber to a second chamber. Upon the expiration of a predetermined time which is based of the rate of flow of the fluid, an indication such as an "expired" indication is displayed by the device. U.S. patent application 20040240324 is incorporated herein in its entirety by reference.

Further, in various industrial applications, human exposure to certain conditions such as a radioactive condition is know be tolerable or acceptable when less than a predetermined exposure and is know to be intolerable or unacceptable when greater than a predetermined exposure. Thus a need to track the duration and quantity of exposure has been identified. In response to such need, various exposure levels monitoring devices and various exposure elapsed time measuring and indication devices have been developed. Examples of such devices are disclosed in U.S. Pat. Nos. 4,903,254, 5,058,088, 5,364,132, 5,446,705, 5,602,804, 5,633,835, 5,699,326, 5,715,215, 5,719,828, 5,785,354, 5,822,280, 5,862,101, 5,873,606, 5,930,206, 5,947,369, 5,957,458, 6,295,252, 6,452,873, and 6,796,065. The listed patents are incorporated herein by reference.

In spite of the advances and advantages of the inventions described above, to the applicant's knowledge, no time indication device exists that is directly connected to routinely used medical devices such as an intravenously inserted tube and needle assembly (IV). It also noted that leaving an IV inserted into a patient beyond a predetermined generally accepted time period is believed to contribute to causing nosocomial infections or phlebitis in the patient. Further no such devices known to prevent use of a medical apparatus without the starting the timing of such timing device. Further, no such devices are known to record the point at which such devices are stopped in their time measuring function.

SUMMARY OF THE INVENTION

The present invention has been developed in response to the present state of the art, and in particular, in response to the medical applications that were described to be lacking in the art. Accordingly, the present invention is adapted to attach directly to an IV or like medical device, is adapted to prevent the use of such medical device without starting the timing function of the invention, and is adapted to stop the timing function and permanently record and display the elapsed usage time of the device for which time is tracked.

The invention comprises a time measuring and indication device that is adapted to be connected to an IV apparatus or like apparatus such as by the device being adhered to the IV or by the device being mechanically attached to the IV apparatus. The time measuring function of the device may be one of a variety of timing measuring functions such as a gas diffusion timing measuring function or an electronic timing measuring function. However, the time measuring function of the device is preferably substantially identically to the time measuring function of the timing device disclosed in U.S. patent application 20040240324. Thus the time measuring and indication device measures time by means of measuring the flow of a fluid having a known fluid flow rate. Before the time measuring and indication device is actuated, a first indicia such as the word "GOOD" is displayed by the device, and after a predetermined lapse of time, a second indicia such as the word "EXPIRED" is displayed by the device.

It is noted that the device may of course be attached to other items such as a substantially broad surface of a catheter or a portion of the device may be wrapped around a tube such as an IV tube. The device may even be attached directly to a patient. The time measuring and indication device further includes a means to halt or stop the time measuring function and to permanently display the elapsed period of time. Such time measurement stopping function is provided by causing a reacting fluid to be introduced to the flow fluid such that the flow of the flow fluid is stopped. The time measuring and indication device further includes a means to prevent use of an apparatus such as an IV apparatus or like medical apparatus to which the time measuring and indication device is attached, without first actuating the time measuring function of the time measuring and indication device. Such use prevention means is provided for instance by housing the time measuring and indication device within a housing assembly. The housing assembly defines a first housing member having a first eyelet and a second housing member having a second eyelet, the assembly of the two housing members defining a housing assembly having at least two eyelets in substantially close proximity to each other, and defining a housing assembly having an inner cavity in which the time measuring and indication device is positioned. A first IV end is retentatively positioned in the first eyelet and a second IV end is retentatively positioned in the second eyelet such that the IV may not be placed into use without separating the IV ends. The time measuring and indication device mounted within the housing assembly is adapted such that if the IV ends are separated, the first housing member slides away from the second housing member, causing a ramp formed in the first housing member to at least partially crush a bulbous activation button, thus causing the initiation of the time measuring function of the time measuring and indication device.

Reference throughout this specification to features, advantages, or similar language does not imply that all of the features and advantages that may necessarily be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

DESCRIPTION OF DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which:

FIG. 1 is a plan view of a first embodiment of a timing apparatus, the timing apparatus is shown in a pre-actuation state;

FIG. 2 is a cross-sectional view of the first embodiment of a timing apparatus shown in FIG. 1;

FIG. 5 is a rear view of a first embodiment of a timing apparatus, the timing apparatus backing is shown unremoved;

FIG. 6 is a rear view of a first embodiment of a timing apparatus, the timing apparatus backing is shown partially peeled back;

FIG. 19 is a trimetric view of a second embodiment of a timed medical apparatus, the apparatus is shown in a pre-actuation state;

FIG. 20 is a cross-sectional view of the apparatus shown in FIG. 19;

DETAILED DESCRIPTION OF THE INVENTION

Figure 3:
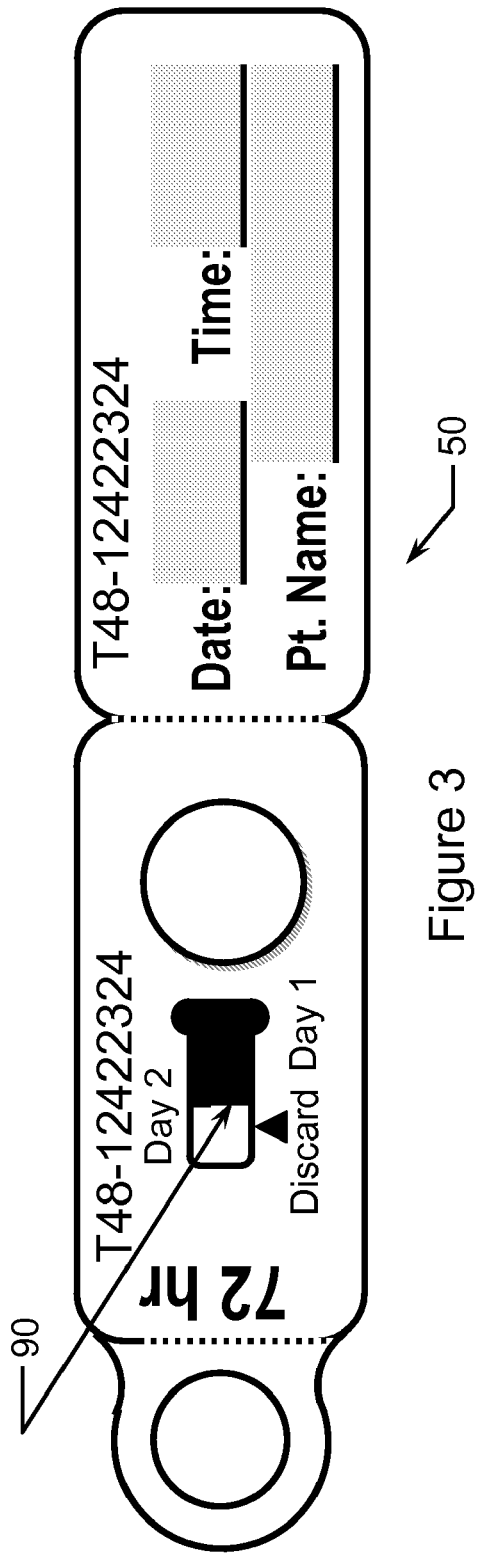
FIG. 3 is a plan view of a first embodiment of a timing apparatus, the timing apparatus is shown in a first post-actuation state.
Figure 4:
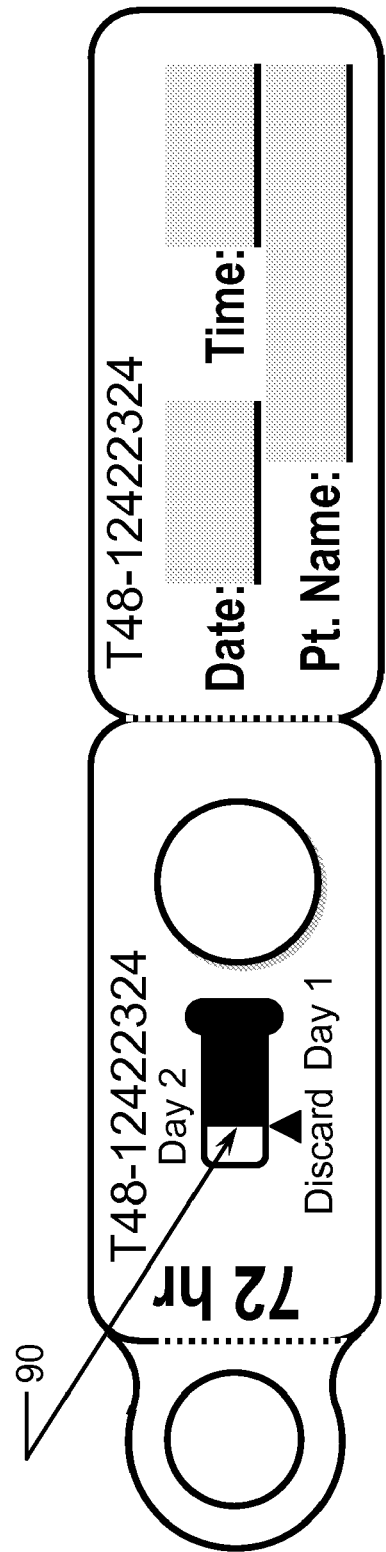
FIG. 4 is a plan view of a first embodiment of a timing apparatus, the timing apparatus is shown in an expired post-actuation state.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are included to provide a thorough understanding of embodiments of the invention. One skilled in the relevant art will recognize, however, that the invention can be practiced without one or more of the specific details, or with other methods, components, materials, and so forth. In other instances, well-known structures, materials, or operations are not shown or described in detail to avoid obscuring aspects of the invention.

The invention is an elapsed time indicating medical apparatus. The invention preferably includes means to assure timing device actuation if placing the medical apparatus in use and means to lock or "freeze" the elapsed time that is indicated at the completion of use of the apparatus. In order to facilitate the understanding of the present invention in reviewing the drawings accompanying the specification, a feature list is provided below. It is noted that like features are like numbered throughout all of the figures.

| FEATURE TABLE | | | |
|---|---|---|---|
| # | Feature | # | Feature |
| 50 | Timing apparatus | 150 | Timing apparatus |
| 52 | Timing apparatus substrate | 152 | Timing apparatus substrate |
| 54 | Timing apparatus adhesive | 154 | Timing apparatus adhesive |
| 56 | Adhesive backing | 156 | Adhesive backing |
| 57 | Peel starter | 157 | Peel starter |
| 60 | Timing apparatus first portion | 160 | Timing apparatus first portion |
| 62 | Timing fluid button | 162 | Timing fluid button |
| 63 | Timing fluid frangible wall | 163 | Timing fluid frangible wall |
| 64 | Timing fluid display window | 164 | Timing fluid display window |
| 66 | Display window graduation marks | 166 | Display window graduation marks |
| 68 | Timing apparatus expiration indicia | 168 | Timing apparatus expiration indicia |
| 70 | Timing apparatus maximum usage indicia | 170 | Timing apparatus maximum usage indicia |
| 72 | Identification indicia first instance | 172 | Identification indicia first instance |
| 74 | Timing apparatus flange | 174 | Timing apparatus flange |
| 76 | Timing apparatus flange hole | 176 | Timing apparatus flange hole |
| 78 | First portion to flange perforated separation line | 178 | First portion to flange perforated separation line |
| 80 | Timing apparatus second portion | 180 | Timing apparatus second portion |
| 82 | Identification indicia second instance | 182 | Identification indicia second instance |
| 84 | Date indication indicia | 184 | Date indication indicia |
| 86 | Time indication indicia | 186 | Time indication indicia |
| 88 | Patient name indication indicia | 188 | Patient name indication indicia |
| 89 | First portion to second portion perforated separation line | 189 | First portion to second portion perforated separation line |
| 90 | Time indication fluid | 190 | Time indication fluid |
| 92 | Warning indicia | 202 | Warning indicia |
| 100 | Elapsed time indicating medical apparatus | 203 | Locking fluid button |
| 101 | Timing apparatus | 204 | Locking fluid |
| 102 | Connection bar | 206 | Locking fluid frangible wall |
| 104 | Timing apparatus third portion | 208 | Solidified dam |
| 106 | Perforated separation line | 210 | Viewing orientation symbol |
| 110 | IV | 270 | Elapsed time indicating medical apparatus |
| 120 | Elapsed time indicating medical apparatus | 280 | Actuator |
| 220 | Elapsed time indicating medical apparatus | 282 | Actuator chamber |
| 230 | Actuator | 284 | First open slot |
| 232 | Actuator chamber | 285 | Second open slot |
| 234 | First open slot | 286 | Ramp |
| 235 | Second open slot | 288 | IV receptacle |
| 236 | Ramp | 300 | Elapsed time indicating medical apparatus |
| 240 | Actuator bar | 304 | Adhesive tape in general |
| 242 | Actuator bar flange | 305 | Adhesive |
| 244 | Actuator bar flange hole | 306 | Tape backing |
| 250 | IV assembly | 307 | Tape peel starter |
| 252 | IV tube | 310 | IV assembly |
| 254 | IV retention flange | 312 | IV tube |
| 260 | Load direction indication arrow | 314 | IV needle in general |
| | | 316 | Needle body |
| | | 318 | Needle tip |
| | | 320 | Actuator |
| | | 322 | Actuator chamber |
| | | 324 | First open slot |
| | | 325 | Second open slot |
| | | 326 | Ramp |

Referring now to the drawings and in particular to FIGS. 1 through 6, a first embodiment of the invention is a timing apparatus 50 for use in timing the duration of use of a medical device comprising a substantially flat, broad, and flexible substrate 52, a layer of adhesive 54, and an adhesive backing or protective cover 56. Adhesive layer 54 is adhesively positioned between substrate 52 back surface and backing 56. Timing apparatus 50 further includes a peel starter 57 located between a portion of adhesive layer 54 and a portion of an adhesive backing 56 and facilitates more ready removal of adhesive backing 56 from adhesive layer 54. Timing apparatus 50 further defines a first portion 60, a second portion 80, and a flange 74. First portion 60 is preferably frangibly connected to second portion 80 on a first end by means of a first portion to second portion perforated separation line 89, and first portion 60 is preferably frangibly connected to flange 74 on a second end by means of a first portion to flange perforated separation line 78.

First portion 60 further includes a timing fluid button 62, a display window 64, display window graduation marks 66, a timing apparatus expiration indicia 68, a timing apparatus maximum usage indicia 70, and an identification indicia first instance 72. Button 62 defines a compressible or crushable button containing display fluid 90. Display window 64 defines a display fluid containable cavity, at least a portion of which is substantially transparent to reveal or display the contents of display window 64. Button 62 is frangibly or rupturably connected to display window 64 by means of frangible wall 63 (not shown) such that compressing or crushing button 62 causes frangible wall 63 to break and display fluid 90 contained in button 62 to initiate flow into window 64 at a predetermined rate. Graduation marks 66 are positioned on window 64 such that the passage of time as measured from the initiation of flow of display fluid 90 is readily trackable or measurable by means of graduation marks 66. It shall be noted however, that graduation marks 66, while useful in assessing the passage of time, are nevertheless optional. Timing apparatus expiration indicia 68 is positioned near window 64 such that when display fluid 90 reaches expiration indicia 68, maximum usage of apparatus 50 is indicated. Alternatively, expiration indicia 68 may be adapted such that expiration indicia 68 is only displayed upon expiration of apparatus 50. Timing apparatus maximum usage indicia 70 is positioned on first portion 60 and indicates the maximum time for which the select apparatus 50 is usable. In the instance of apparatus 50 shown in FIG. 1, the 72 hour indicia is merely exemplary and may be more or less than 72 hours. Identification indicia first instance 72 is positioned on first portion 60 and defines an indicia unique to the instance of the apparatus 50.

Second portion 80 further includes an identification indicia second instance 82, a date indicia 84, a time indicia 86, and a patient name indication indicia 88. Identification indicia second instance 82, which is substantially identical to identification first instance 72, is positioned on second portion 80 and may be used to associate first portion 60 with second portion 80 when first portion 60 is separated from second portion 80. Date indicia 84, time indicia 86, and patient name indication indicia 88 are all positioned on second portion 80 and each provide an area that may be written upon so as to identify a date, time, and patient with which the use of apparatus 50 is associated. Additionally, other indicia preferably having a writable area associated with the other indicia may also be added to portion 80.

Flange 74 further includes a flange hole 76 for use in attaching apparatus 50 to a medical device. Adhesive backing 56 further preferably includes a warning indicia 92 positioned on an external surface of backing 56 such that a user of apparatus 50 may readily be warned with a warning such as a warning regarding the capabilities and proper usage of apparatus 50.

In practice, apparatus 50 is attached to an IV or like medical device by positioning a tube of an IV through flange hole 76. Upon insertion of the IV into a patient, button 62 is compressed causing the initiation of flow of display fluid 90 from button 62 to window 64. The user also writes or otherwise marks on portion 80, the date and time of usage initiation of apparatus 50 and the name of the patient on whom apparatus 50 is used. Such marking will typically be performed after initiation of use of apparatus 50 but may alternatively be marked immediately prior to initiation of use of apparatus 50. Usage of apparatus being thus initiated and markings being marked, apparatus 50 provides a sure means whereby the elapsed time of usage of apparatus 50 can be monitored and observed. With apparatus 50 thus monitoring elapsed time of usage corresponding to the duration of insertion of an IV or like medical device, excessive or undue prolonged insertion of an IV or like medical device is prevented. Upon completion of the time tracking function, apparatus 50 may be removed from an IV by tearing perforated separation line 78. Adhesive backing 56 is then removed from adhesive layer 54, and the remainder of apparatus 50 may be adhered to the paper medical record or like medical information tracking device corresponding to the patient on whom apparatus 50 was used. It is further noted that alternatively, only portion 60 or only portion 80 may be applied to the paper medical record or like medical information tracking device. Thus apparatus 50 further provides a permanent record of the duration of use of apparatus 50 and the corresponding medical device for which apparatus 50 tracked time usage.

Figure 7:
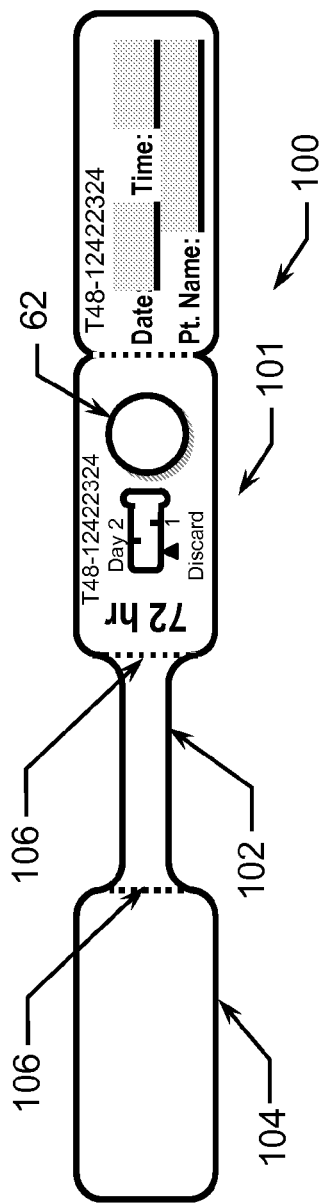
FIG. 7 is a plan view of a second embodiment of a timing apparatus.
Figure 8:
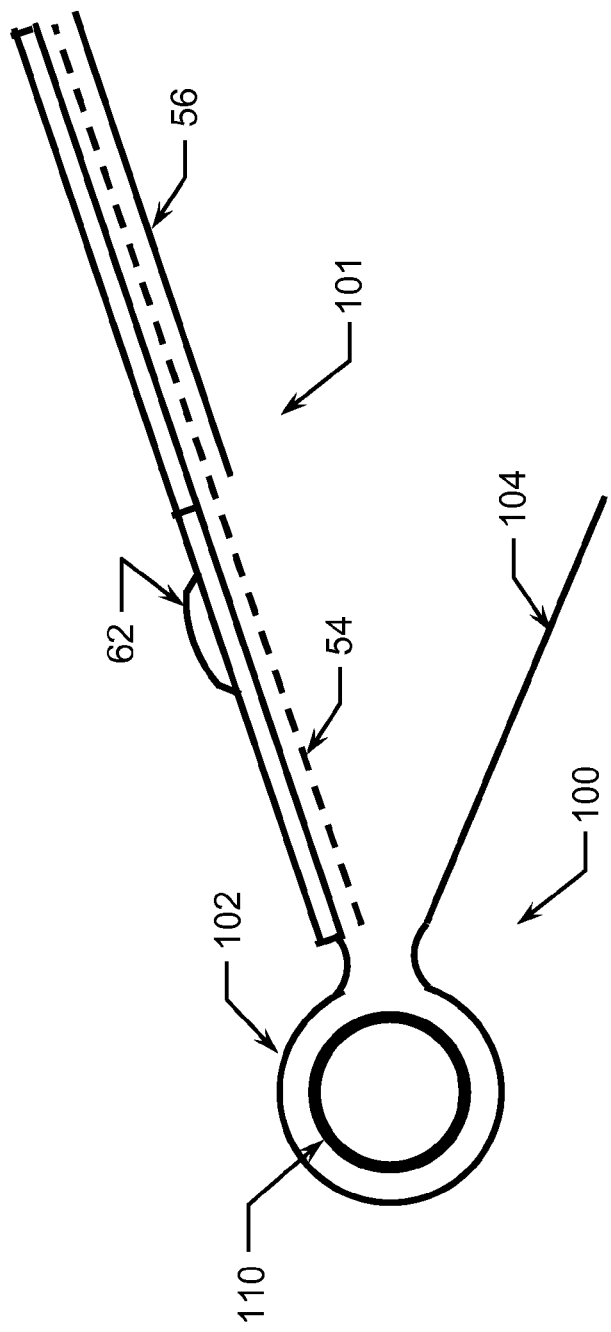
FIG. 8 is a cross-sectional view of the embodiment shown in FIG. 7 except that the apparatus is shown partially wrapped around and adhered to an IV tube.

Referring now to the drawings and in particular to FIGS. 7 and 8, a second embodiment of the invention is an elapsed time indicating medical apparatus 100 for use in timing the duration of use of medical apparatus 100. Apparatus 100 comprises timing apparatus 101 and IV 110. Apparatus 101 is substantially identical to and operates substantially identical to apparatus 50 except that in apparatus 101 flange 74 is replaced by connection bar 102 and third portion 104, and perforated separation line 78 is replaced with perforated separation lines 106. Third portion 104 defines a portion that is geometrically similar to first portion 60 and to second portion 80. Connection bar 102 connects to second portion 60 on a first end and to third portion 104 on a second end. Rather than connecting timing apparatus 101 to IV 110 by a means of a flange as in apparatus 50, timing apparatus 101 is adhered to IV 110 by wrapping connecting bar 102 around IV 110, removing a portion of backing 56 from second portion 60, adhering third portion 104 to second portion 60. After the timing function of timing apparatus 101 is complete, timing apparatus 101 is removed from IV 110 by tearing perforated separation lines 106. Adhesive backing 56 is then removed from the remainder of adhesive layer 54, and the remainder of apparatus 101 may be adhered to the paper medical record or like medical information tracking device corresponding to the patient on whom apparatus 100 was used.

Figure 9:
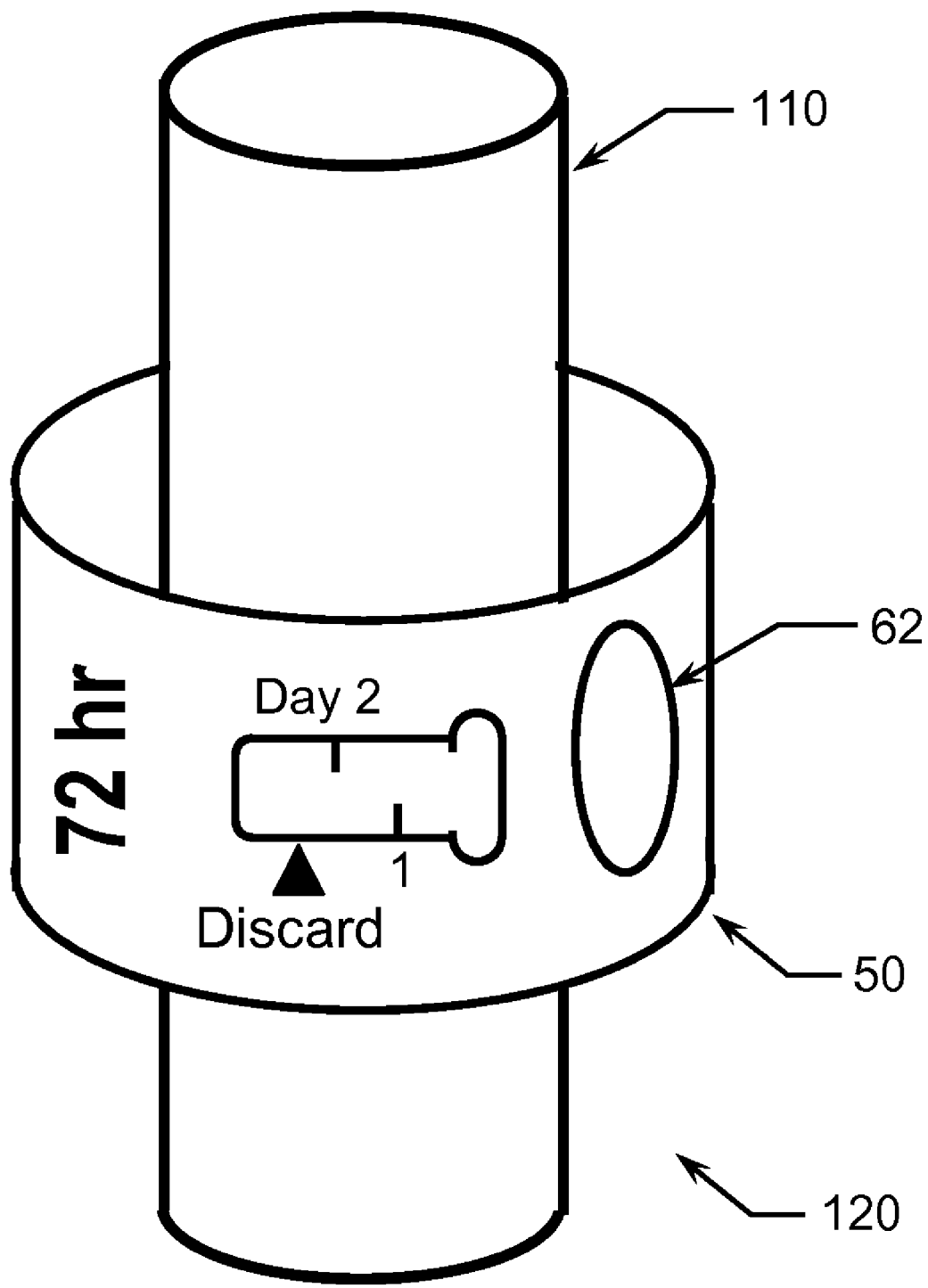
FIG. 9 is a trimetric view of the timing apparatus shown in FIG. 1 except that the apparatus is shown wrapped substantially completely around and adhered to an IV tube.
Figure 10:
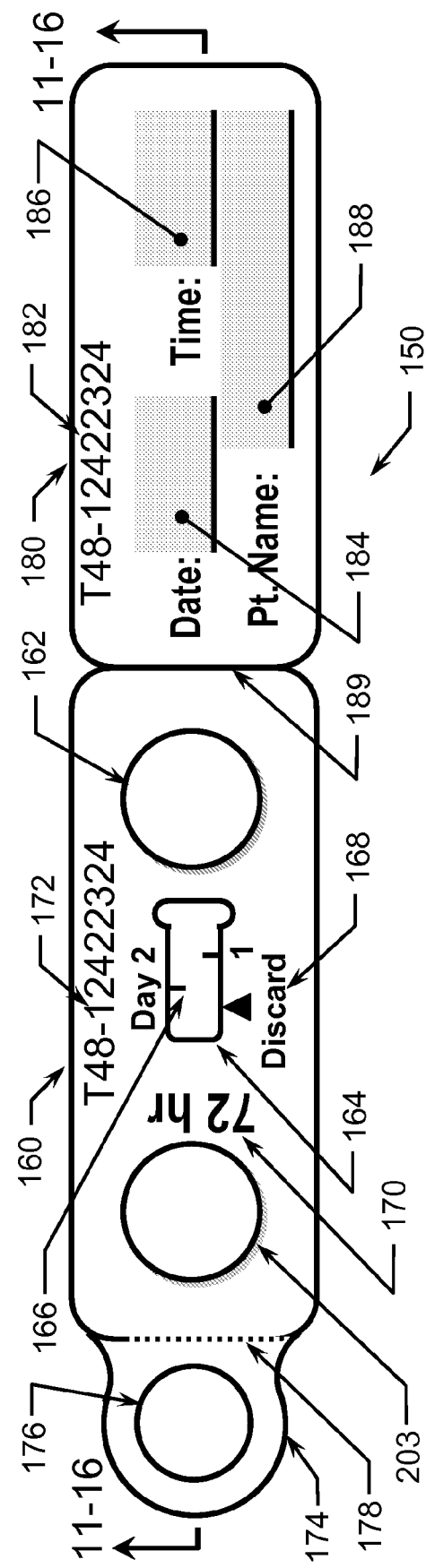
FIG. 10 is a plan view of a third embodiment of a timing apparatus.
Figure 11:
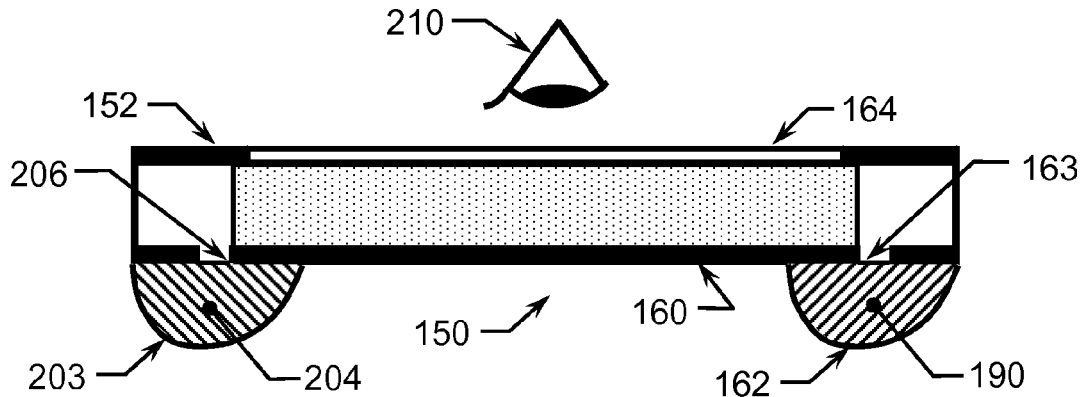
FIG. 11 is a schematic cross-sectional view of the first portion of the timing apparatus shown in FIG. 10, item 210 indicates the view direction in which a user would view the apparatus and the timing apparatus is shown in a pre-actuation state.
Figure 12:
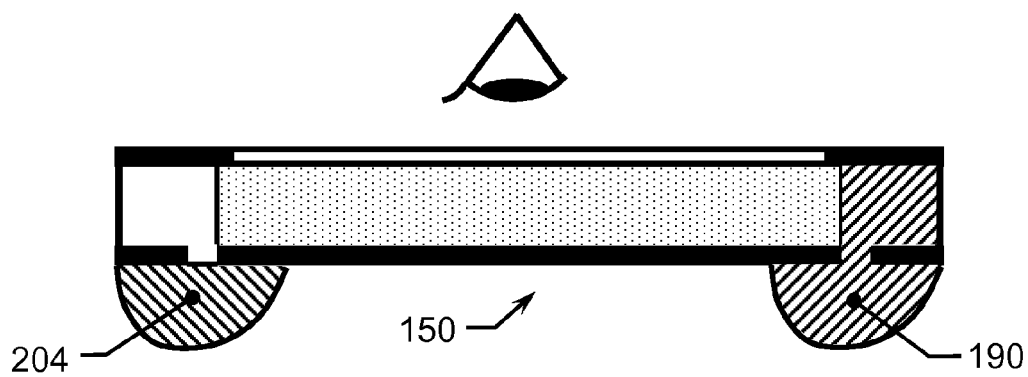
FIG. 12 is a schematic cross-sectional view of the first portion of the timing apparatus shown in FIG. 10, the timing apparatus is shown in a first timing post-actuation state.
Figure 13:
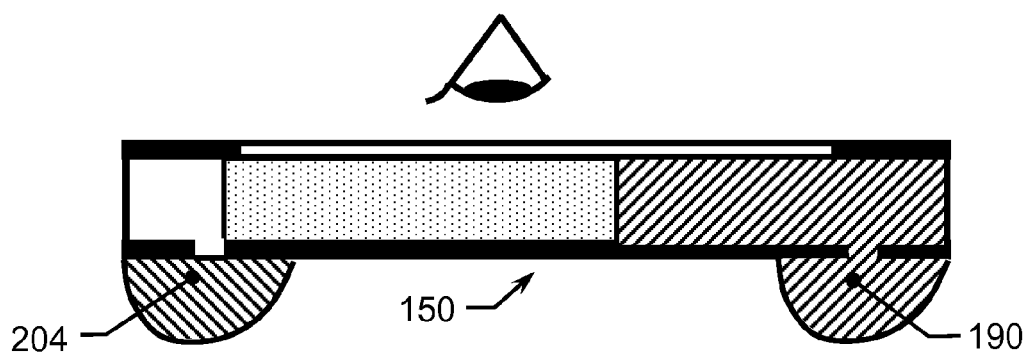
FIG. 13 is a schematic cross-sectional view of the first portion of the timing apparatus shown in FIG. 10, the timing apparatus is shown in a second timing post-actuation state.
Figure 14:
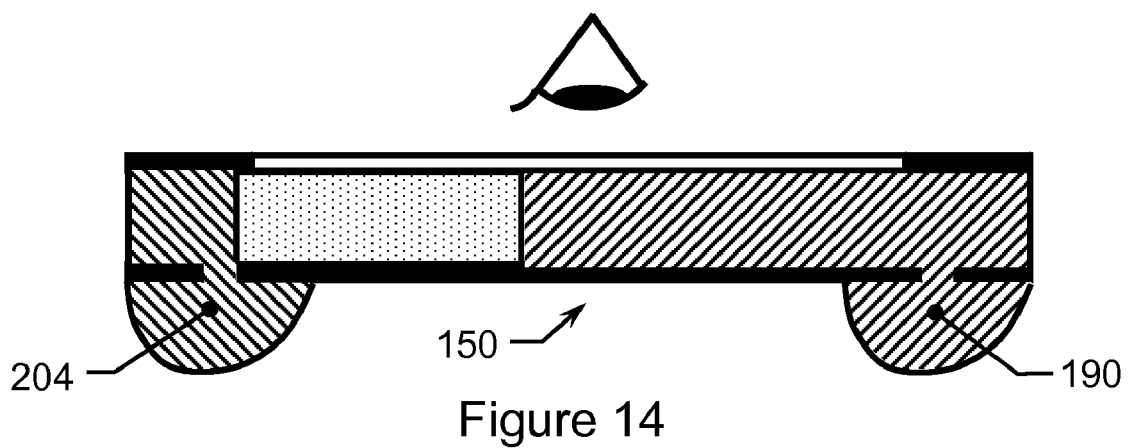
FIG. 14 is a schematic cross-sectional view of the first portion of the timing apparatus shown in FIG. 10, the timing apparatus is shown in a first lock post-actuation state.
Figure 15:
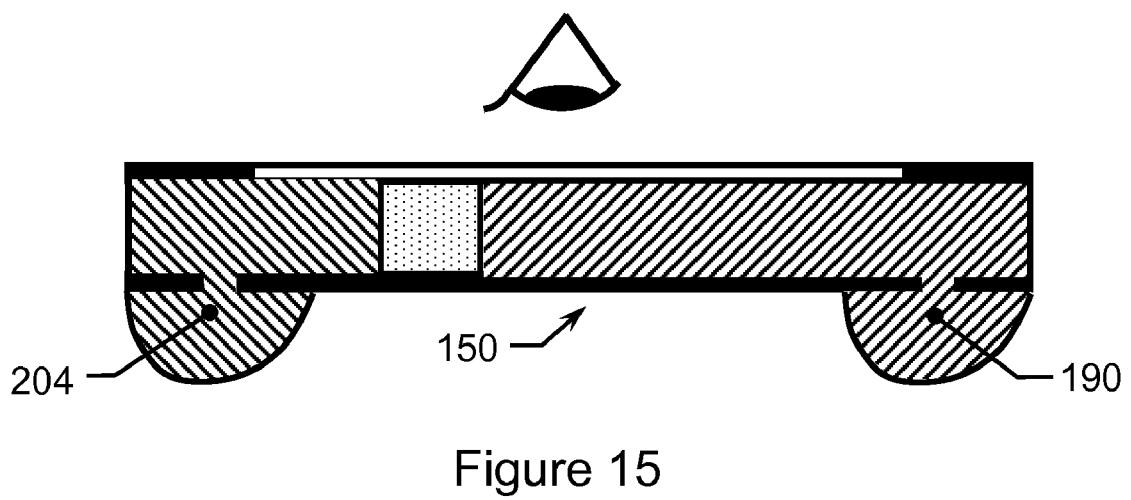
FIG. 15 is a schematic cross-sectional view of the first portion of the timing apparatus shown in FIG. 10, the timing apparatus is shown in a second lock post-actuation state.
Figure 16:
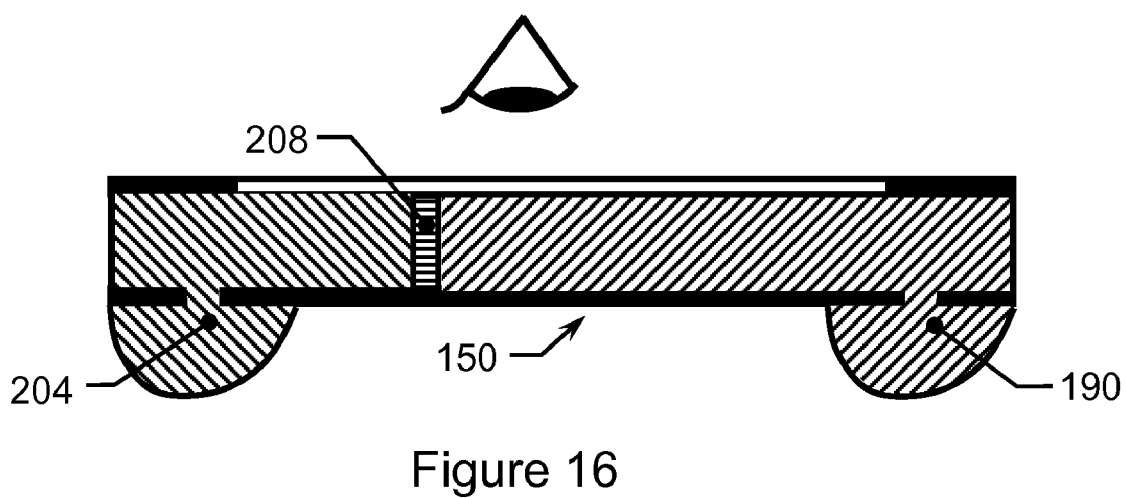
FIG. 16 is a schematic cross-sectional view of the first portion of the timing apparatus shown in FIG. 10, the timing apparatus is shown in a final lock post-actuation state.

Referring now to the drawings and in particular to FIG. 9, a third embodiment of the invention is an elapsed time indicating medical apparatus 120 for use in timing the duration of use of medical apparatus 120. In this embodiment, apparatus 50 preferably remains permanently adhered to IV 110. It is noted however, that apparatus 50 alternatively forms a ring as shown in FIG. 9 but apparatus 50 is not adhered to IV 110 but rather is mechanically retained to IV 110 such as by a groove in IV 110 or by an IV retaining flange or the like.

Referring now to the drawings and in particular to FIGS. 10 through 16, a fourth embodiment of the invention is a timing apparatus 150 for use in timing the duration of use of a medical device comprising a substantially flat, broad, and flexible substrate 152, a layer of adhesive 154 (not shown), and an adhesive backing or protective cover 156 (not shown). Adhesive layer 154 is adhesively positioned between substrate 152 back surface and backing 156. Timing apparatus 150 further includes a peel starter 157 (not shown) located between a portion of adhesive layer 154 and a portion of an adhesive backing 156 and facilitates more ready removal of adhesive backing 156 from adhesive layer 154. Timing apparatus 150 further defines a first portion 160, a second portion 180, and a flange 174. First portion 160 is preferably frangibly connected to second portion 180 on a first end by means of a first portion to second portion perforated separation line 189, and first portion 160 is preferably frangibly connected to flange 74 on a second end by means of a first portion to flange perforated separation line 78.

First portion 160 further includes a timing fluid button 162, a display window 164, display window graduation marks 166, a timing apparatus expiration indicia 168, a timing apparatus maximum usage indicia 170, an identification indicia first instance 172, a locking fluid button 203, and a locking fluid frangible wall. Button 162 defines a compressible or crushable button containing display fluid 190. Display window 164 defines a display fluid and a locking fluid containable cavity, at least a portion of which is substantially transparent to reveal or display the contents of display window 164. Button 203 defines a compressible or crushable button containing locking fluid 204. Button 162 is frangibly or rupturably connected to display window 164 by means of frangible wall 163 such that compressing or crushing button 162 causes frangible wall 163 to break and display fluid 190 contained in button 162 to initiate flow into window 164 at a predetermined rate. Further, button 203 is frangibly or rupturably connected to display window 164 by means of frangible wall 206 such that compressing or crushing button 203 causes frangible wall 206 to break and locking fluid 204 contained in button 203 to initiate flow into window 164 at a predetermined rate. Locking fluid 204 preferably flows at a much faster rate than display fluid 190. When display fluid 190 comes into contact with locking fluid 204, a solidification of at least a portion of the fluids occurs, solidified dam 208 is formed, and display fluid 190 is substantially stopped in its progress to substantially permanently record the fixed elapsed time. Solidified dam 208 may alternatively define a non-solidified dam such as a high viscosity gel dam so long as dam 208 functions to stop the migrations of display fluid 190. Display fluid 190 and locking fluid 204 may be any of a broad number of reacting type fluids. For instance, display fluid 190 may be water when locking fluid 204 is cyanoacrylate (which cures upon contact with water). Alternatively display fluid 190 may be an adhesive in anaerobic environment (which cures upon contact with air) when locking fluid 204 is air. To better distinguish between display fluid 190 and locking fluid 204, display fluid 190 may be of a different color than locking fluid 204 and the fluids may be of substantially contrasting colors. Graduation marks 166 are positioned on window 164 such that the passage of time as measured from the initiation of flow of display fluid 190 is readily trackable or measurable by means of graduation marks 166. It shall be noted however, that graduation marks 166, while useful in assessing the passage of time, are nevertheless optional. Timing apparatus expiration indicia 168 is positioned near window 164 such that when display fluid 190 reaches expiration indicia 168, maximum usage of apparatus 150 is indicated. Alternatively, expiration indicia 168 may be adapted such that expiration indicia 168 is only displayed upon expiration of apparatus 150. Timing apparatus maximum usage indicia 170 is positioned on first portion 160 and indicates the maximum time for which the select apparatus 150 is usable. In the instance of apparatus 150 shown in FIG. 10, the 72 hour indicia is merely exemplary and may be more or less than 72 hours. Identification indicia first instance 172 is positioned on first portion 160 and defines an indicia unique to the instance of the apparatus 150.

Second portion 180 further includes an identification indicia second instance 182, a date indicia 184, a time indicia 186, and a patient name indication indicia 188. Identification indicia second instance 182, which is substantially identical to identification first instance 172, is positioned on second portion 180 and may be used to associate first portion 160 with second portion 180 when first portion 160 is separated from second portion 180. Date indicia 184, time indicia 186, and patient name indication indicia 188 are all positioned on second portion 180 and each provide an area that may be written upon so as to identify a date, time, and patient with which the use of apparatus 150 is associated. Additionally, other indicia preferably having a writable area associated with the other indicia may also be added to portion 80.

Flange 174 further includes a flange hole 176 for use in attaching apparatus 150 to a medical device. Adhesive backing 156 further preferably includes a warning indicia 202 (not shown) positioned on an external surface of backing 156 such that a user of apparatus 150 may readily be warned with a warning such as a warning regarding the capabilities and proper usage of apparatus 150.

In practice, apparatus 150 is attached to an IV or like medical device by positioning a tube of an IV through flange hole 176. Upon insertion of the IV into a patient, button 162 is compressed causing the initiation of flow of display fluid 190 from button 162 to window 164. The user also writes or otherwise marks on portion 180, the date and time of usage initiation of apparatus 150 and the name of the patient on whom apparatus 150 is used. Such marking will typically be performed after initiation of use of apparatus 150 but may alternatively be marked immediately prior to initiation of use of apparatus 150. Usage of apparatus being thus initiated and markings being marked, apparatus 150 provides a sure means whereby the elapsed time of usage of apparatus 150 can be monitored and observed. With apparatus 150 thus monitoring elapsed time of usage corresponding to the duration of insertion of an IV or like medical device, excessive or undue prolonged insertion of an IV or like medical device is prevented. Upon completion of usage of the IV or like corresponding medical device, button 203 is compressed causing the initiation of flow of locking fluid 204 from button 203 to window 164 and further causes solidified dam 208 to form and substantially "locks" the elapsed time. After "locking" the elapsed time, apparatus 150 may be removed from an IV by tearing separation line 178. Adhesive backing 156 is then removed from adhesive layer 154, and the remainder of apparatus 150 may be adhered to the paper medical record or like medical information tracking device corresponding to the patient on whom apparatus 150 was used. It is further noted that alternatively, only portion 160 or only portion 180 may be applied to the paper medical record or like medical information tracking device. Thus apparatus 150 further provides a permanent record of the duration of use of apparatus 150 and the corresponding medical device for which apparatus 150 tracked time usage.

Figure 17:
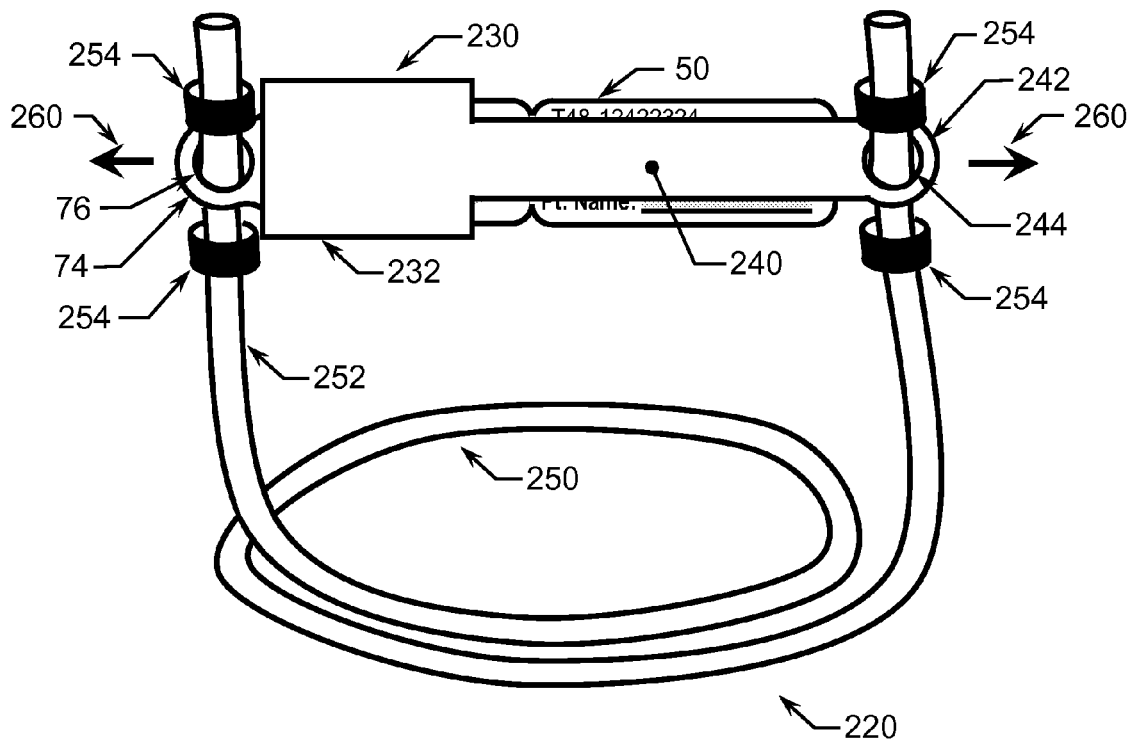
FIG. 17 is a trimetric view of a first embodiment of a timed medical apparatus, the apparatus is shown in a pre-actuation state.
Figure 18:
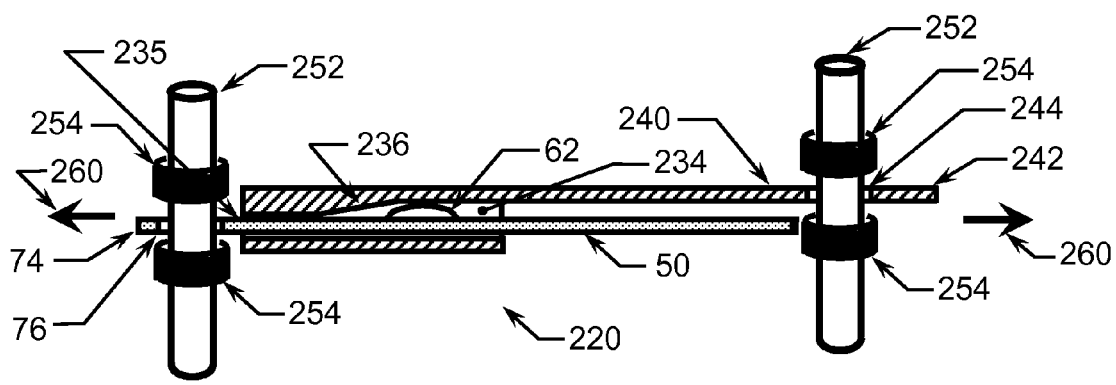
FIG. 18 is a cross-sectional view of the apparatus shown in FIG. 17 except that the IV assembly is not shown as cut away and only the ends of the IV assembly are shown, the apparatus is shown in a pre-actuation state.

Referring now to the drawings and in particular to FIGS. 17 and 18, a fifth embodiment of the invention is an elapsed time indicating medical apparatus 220 for use in timing the duration of use of medical apparatus 220. Apparatus 220 comprises timing apparatus 50, IV assembly 250, and actuator 230. Actuator 230 comprises an elongated actuator body having an actuator chamber 232, a first open slot 234, a second open slot 235, a ramp 236, a bar 240, a bar flange 242, and a bar flange hole 244. First open slot 234 is located on a first end of chamber 232 and second open slot 235 is located on a second end of chamber 232. Ramp 236 is located within chamber 232. A first end of bar 240 is connected to a second end of chamber 232, and flange 242 is connected to a second end of bar 240. Flange hole 244 is centrally located within flange 242. IV assembly 250 includes an IV tube 252 and a plurality of IV tube retention flanges 254. IV retention tube 252 defines an IV tube having a first end and a second end with each of tube 252 ends having a pair of IV retention flanges 254 retentatively connected to tube 252. Each pair of retention flanges 254 forming a gap therebetween. Medical apparatus 220 is assembled such that button 62 of timing apparatus 50 is positioned within actuator chamber 232 in near proximity to ramp 236 and such that first portion 60 protrudes out of first open slot 234 and such that flange 74 protrudes out of second open slot 235. Medical apparatus 220 is further assembled such that a first end of IV tube 252 passes through flange hole 76, with flange 74 being retentatively positioned within a gap formed between two IV retention flanges 254 and such that a second end of IV tube 252 passes through actuator bar flange hole 244, with flange 242 being retentatively positioned within a gap formed between two IV retention flanges 254. It is noted that flange 74 and flange 242 may be alternatively secured to IV tube 252 such as by means of a compression fit between each of flanges 74 and 242 and IV 252 or by means of at least one retaining groove formed in IV 252.

In practice, in order to initiate use of medical apparatus 220, the ends of IV tube 252 must be separated. Separating the ends of IV tube 252 requires the application of two opposing forces applied in the direction of load direction indication arrows 260. Such application of load in turn causes button 62 to be forced against and compressed by ramp 236 in actuator chamber 232 prior to timing apparatus 50 being withdrawn from actuator 230. Thus by means of the described process, timing apparatus 50 of medical apparatus 220 is automatically initiated upon the separation of the end of IV tube 252. Further, it is seen that without separating the ends of IV tube 252 and the resultant automatic initiation of timing device 50, medical apparatus 220 is unable to be placed into use.

Referring now to the drawings and in particular to FIGS. 19 and 20, a sixth embodiment of the invention is an elapsed time indicating medical apparatus 270 for use in timing the duration of use of medical apparatus 270. Apparatus 270 comprises timing apparatus 50, IV assembly 250, and actuator 280. Actuator 280 comprises an elongated actuator body having an actuator chamber 282, a first open slot 284, a second open slot 285, a ramp 286, and an IV receptacle 288. First open slot 284 is located on a first end of chamber 282 and second open slot 285 is located on a second end of chamber 282. Ramp 286 is located within chamber 282. IV receptacle 288 defines an additional cavity formed within actuator 280. IV assembly 250 includes an IV tube 252 and at least one IV tube retention flange 254. Medical apparatus 270 is assembled such that button 62 of timing apparatus 50 is positioned within actuator chamber 282 in near proximity to ramp 286 and such that first portion 60 protrudes out of first open slot 284 and such that flange 74 protrudes out of second open slot 285. Medical apparatus 270 is further assembled such that a first end of IV tube 252 passes through flange hole 76 and such that IV tube 252 first end is housed within IV receptacle 288. Flange 74 is further retentatively positioned adjacent at least one IV retention flange 254 such that IV tube 252 first end may not be removed from IV receptacle 288 but that a load is applied to flange 74 by at least one retention flange 254.

In practice, in order to initiate use of medical apparatus 270, the first end of IV tube 252 must be exposed by removing the first end of tube 252 from IV receptacle 288. Such removal of tube 252 first end from receptacle 288 requires the application of two opposing forces applied in the direction of load direction indication arrows 260. Such application of load in turn causes button 62 to be forced against and compressed by ramp 286 in actuator chamber 282 prior to timing apparatus 50 being withdrawn from actuator 280. Thus by means of the described process, timing apparatus 50 of medical apparatus 270 is automatically initiated upon the removal of tube 252 first end from receptacle 288. Further, it is seen that without removing tube 252 first end from receptacle 288 and the resultant automatic initiation of timing device 50, medical apparatus 270 is unable to be placed into use.

Figure 21:
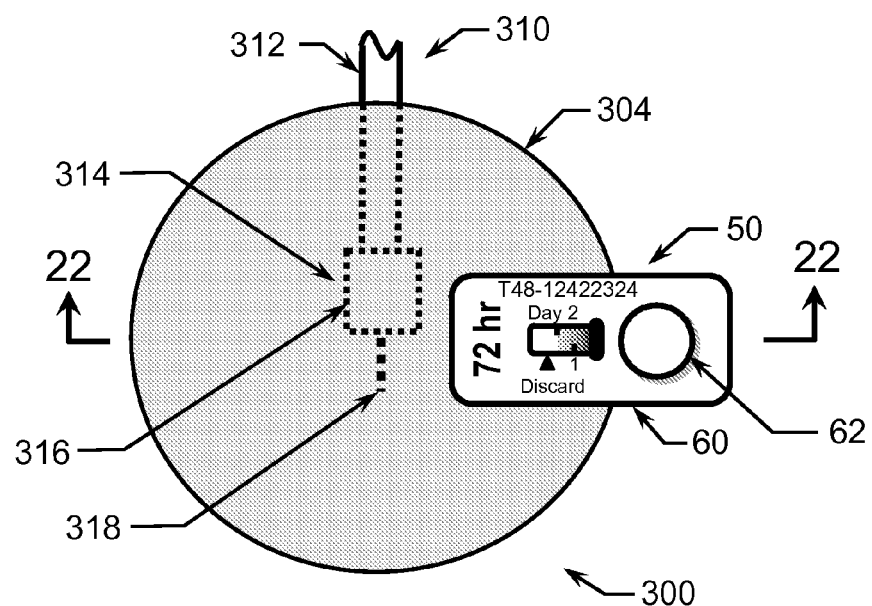
FIG. 21 is a plan view of a third embodiment of a timed medical apparatus, only portion 60 of timing apparatus 50 is shown and medical apparatus is shown with the actuator removed and the apparatus in a post-actuation state.
Figure 22:
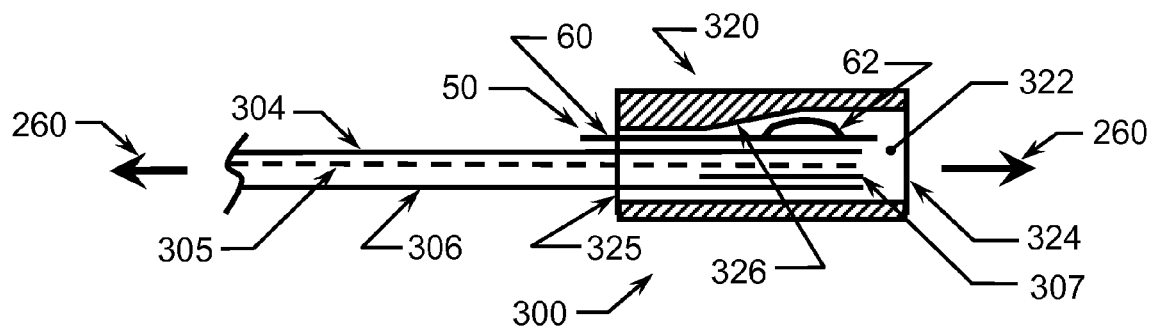
FIG. 22 is a cross-sectional view of the apparatus shown in FIG. 21, the IV assembly is not shown and the actuator is shown in-place with the apparatus in a pre-actuation state.

Referring now to the drawings and in particular to FIGS. 21 and 22, a seventh embodiment of the invention is an elapsed time indicating medical apparatus 300 for use in timing the duration of use of medical apparatus 300. Apparatus 300 comprises timing apparatus 50, adhesive tape 304, IV assembly 310, and actuator 320. Adhesive tape 304 defines a preferably disk shaped piece of adhesive tape but may alternatively be an adhesive tape form in a different shape. Adhesive tape 304 further includes a layer of adhesive 305 laminated between tape 304 and a tape backing 306. Tape 304 also includes a tape peel starter 307 positioned between a portion of adhesive layer 305 and a portion of tape backing 306 such that where peel starter 307 lies between tape 304 and backing 306, backing 306 is not adhered to tape 304. Tape backing 306 defines substantially the same footprint of perimeter shape as tape 304 such that removal of tape backing 306 from tape 304 is substantially difficult without the use of tape peel starter 307. IV assembly 310 includes an IV tube 312 connected to an IV needle 314. IV needle 314 further defines a needle body 316 connected to a needle tip 318. Actuator 320 comprises an elongated actuator body having an actuator chamber 322, a first open slot 324, a second open slot 325, and a ramp 326. First open slot 324 is located on a first end of chamber 322 and second open slot 325 is located on a second end of chamber 322. Ramp 326 is located within chamber 322. Medical apparatus 270 is assembled such that button 62 of timing apparatus 50 is positioned within actuator chamber 282 in near proximity to ramp 286 and such that first portion 60 protrudes out of first open slot 284 and such that flange 74 protrudes out of second open slot 285. Medical apparatus 300 is further assembled such that timing apparatus 50 is adhered to tape 304 and such that timing apparatus 50 and tape 304 are positioned within actuator 320.

In practice, IV needle tip 318 is inserted into a patient and tape 304, with timing apparatus 50 adhered to tape 304, has backing 306 removed from tape 304 and tape 304 is placed over at least a portion of IV assembly 310 and a portion of the patient's body in near proximity to the needle tip 318 insertion site, to help retain IV assembly 310 in a proper position. However, in order to remove tape backing 306 from tape 304, actuator 320 must be removed from timing device 50 in order to expose tape peel starter 307. Removal of actuator 320 requires the application of two opposing forces applied in the direction of load direction indication arrows 260. Such application of load in turn causes button 62 to be forced against and compressed by ramp 326 in actuator chamber 322 prior to timing apparatus 50 being withdrawn from actuator 320. Thus by means of the described process, timing apparatus 50 of medical apparatus 300 is automatically initiated upon the removal of actuator 320 from timing apparatus 50 and tape 304. Further, it is seen that without removing timing apparatus 50 and tape 304 from actuator 320, medical apparatus 300 is unable to be placed into use.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

I claim:

1. An elapsed time measuring and indicating insertable medical apparatus for inserting into a patient, said apparatus comprising a fluid dispensing non-pressurized-inflation medical device having an insertable portion and a non-insertable portion, said insertable portion being at least partially inserted within a patient and said non-insertable portion protruding from a patient; and an elapsed time measuring and indication device attached to said non-insertable portion of said medical device, and wherein said time measuring and indication device is adapted to measure and display the duration of elapsed time that said insertable portion remains inserted in a patient, and wherein insertion of said insertable portion into a patient is prevented if said time measuring and indication device is not actuated.

2. The apparatus of claim 1, wherein said time measuring and indication device includes at least one indicia that is substantially unique to an instance of said time measuring and indication device.

3. The apparatus of claim 1, wherein initiation of insertion of said insertable portion into a patient causes said time measuring and indication device to begin to measure and display elapsed time of use of said medical device.

4. The apparatus of claim 1, wherein if said time measuring and indication device is actuated and subsequently stopped, said time measuring and indication device indicates that amount of time that elapsed while said insertable portion was inserted into a patient.

5. The apparatus of claim 1, wherein said time measuring and indication device defines a displayed container containing at least one display fluid having a predetermined rate of flow and wherein said time measuring and indication device measures elapsed time corresponding to a predetermined amount of flow of said at least one display fluid.

6. The apparatus of claim 1, wherein said time measuring and indication device includes a first portion having a first indicia and a second portion having a second indicia, and wherein said first portion and said second portion are separated by a frangible connection member, and wherein said first indicia and said second indicia are substantially unique to an instance of said time measuring and indication device, and wherein said first indicia and said second indicia are substantially similar such that even if said second portion is removed from said first portion said second portion is identifiable as being associated with said first portion.

7. The apparatus of claim 1, wherein said insertable portion further defines an intravenously insertable needle having at least one fluid flow channel within said needle, said flow channel of said needle being capable of transmitting fluids, and wherein said non-insertable portion defines a substantially hollow tubular member capable of transmitting fluids connected to a fluid storage container, said storage container being capable of storing a fluid for transmission to a patient.

8. The medical apparatus of claim 1, wherein said medical device further defines a non-pneumatic medical device.

9. The medical apparatus of claim 1, wherein said medical device further defines an IV.

10. An elapsed time measuring and indicating medical apparatus, said apparatus comprising a fluid dispensing non-pressurized-inflation medical device and an actuatable elapsed time measuring and indication device attached to said medical device, and wherein said time measuring and indication device is adapted to measure and display the duration of time that said medical device is in use, and wherein a predetermined use of said medical device is prevented if said time measuring and indication device is not actuated, and wherein said medical device further defines an intravenously insertable medical device comprising an intravenously insertable needle having at least one fluid flow channel within said needle, said flow channel of said needle being capable of transmitting fluids, and wherein said non-insertable portion defines a substantially hollow tubular member capable of transmitting fluids connected to a fluid storage container, said storage container being capable of storing a fluid for transmission to a patient, and wherein said needle is at least partially inserted within a patient, and wherein insertion of said needle into a patient is prevented if said time measuring and indication device is not actuated.

11. The apparatus of claim 10, wherein initiation of use of said medical device causes said time measuring and indication device to begin to measure and display elapsed time of use of said medical device.

12. The apparatus of claim 10, wherein if said time measuring and indication device is actuated and subsequently stopped, said time measuring and indication device indicates the amount of time that elapsed while said medical device was in use.

13. The apparatus of claim 10, wherein said time measuring and indication device defines a displayed container containing at least one fluid having a predetermined rate of flow and wherein said time measuring and indication device measures elapsed time corresponding to a predetermined amount of flow of said at least one fluid.

14. The apparatus of claim 10, wherein said time measuring and indication device includes a first portion having a first indicia and a second portion having a second indicia, and wherein said first portion and said second portion are separated by a frangible connection member, and wherein said first indicia and said second indicia are substantially unique to an instance of said time measuring and indication device, and wherein said first indicia and said second indicia are substantially similar such that even if said second portion is removed from said first portion said second portion is identifiable as being associated with said first portion.

15. The medical apparatus of claim 10, wherein said medical device further defines a non-pneumatic medical device.

16. The medical apparatus of claim 10, wherein said medical device further defines an IV.

17. An elapsed time measuring and indicating medical apparatus, said apparatus comprising a fluid dispensing non-pressurized-inflation medical device and an actuatable and stoppable elapsed time measuring and indication device attached to said medical device, and wherein said measuring and indication device is adapted to measure and display the duration of time that said medical device is in use, and wherein if said time measuring and indication device is actuated and subsequently stopped, said time measuring and indication device indicates the amount of time that elapsed while said medical device was in use, and wherein said medical device further defines an intravenously insertable medical device comprising an intravenously insertable needle having at least one fluid flow channel within said needle, said flow channel of said needle being capable of transmitting fluids, and wherein said non-insertable portion defines a substantially hollow tubular member capable of transmitting fluids connected to a fluid storage container, said storage container being capable of storing a fluid for transmission to a patient, and wherein said needle is at least partially inserted within a patient, and wherein insertion of said needle into a patient is prevented if said time measuring and indication device is not actuated.

18. The apparatus of claim 17, wherein initiation of use of said medical device causes said time measuring and indication device to begin to measure and display elapsed time of use of said medical device.

19. The apparatus of claim 17, wherein said time measuring and indication device defines a displayed container containing at least one display fluid having a predetermined rate of flow and wherein said time measuring and indication device measures elapsed time corresponding to a predetermined amount of flow of said at least one display fluid.

20. The apparatus of claim 17, wherein said time measuring and indication device includes a first portion having a first indicia and a second portion having a second indicia, and wherein said first portion and said second portion are separated by a frangible connection member, and wherein said first indicia and said second indicia are substantially unique to an instance of said time measuring and indication device, and wherein said first indicia and said second indicia are substantially similar such that even if said second portion is removed from said first portion said second portion is identifiable as being associated with said first portion.

21. The apparatus of claim 17, wherein said time measuring and indication device includes at least one indicia that is substantially unique to an instance of said time measuring and indication device.

22. The apparatus of claim 21, wherein initiation of insertion of said needle into a patient causes said time measuring and indication device to begin to measure and display elapsed time of use of said medical device.

23. The medical apparatus of claim 17, wherein said medical device further defines a non-pneumatic medical device.

24. The medical apparatus of claim 17, wherein said medical device further defines an IV.

25. An elapsed time measuring and indicating insertable medical apparatus for inserting into a patient, said apparatus comprising:
 a medical device having an insertable portion and a non-insertable portion, said insertable portion defining an intravenously insertable needle having at least one fluid flow channel within said needle, said flow channel of said needle being capable of transmitting fluids, and said non-insertable portion defining a substantially hollow tubular member capable of transmitting fluids connected to a fluid storage container, said storage container being capable of storing a fluid for transmission to a patient, and wherein said needle is at least partially inserted within a patient; and
 an actuatable and stoppable elapsed time measuring and indication device attached to said non-insertable portion of said medical device, and wherein said time measuring and indication device is adapted to measure and display the duration of time that said needle is inserted into a patient, and wherein insertion of said needle into a patient is prevented if said time measuring and indication device is not actuated, and wherein initiation of insertion of said needle into a patient causes said time measuring and indication device to begin to measure and display elapsed time of insertion of said needle into a patient, and wherein if said time measuring and indication device is actuated and subsequently stopped, said time measuring and indication device indicates the amount of time that elapsed while said needle was inserted in a patient, and wherein said time measuring and indication device defines a displayed container containing at least one display fluid having a predetermined rate of flow and wherein said time measuring and indication device measures elapsed time corresponding to a predetermined amount of flow of said at least one display fluid;
 and wherein said time measuring and indication device is adhered to said medical device.

26. An elapsed time measuring and indicating medical apparatus, said apparatus comprising a medical device and an actuatable elapsed time measuring and indication device attached to said medical device, and wherein said time measuring and indication device is adapted to measure and display the duration of time that said medical device is in use, and wherein a predetermined use of said medical device is prevented if said time measuring and indication device is not actuated, and wherein said time measuring and indication device includes a first portion having a first indicia and a second portion having a second indicia, and wherein said first portion and said second portion are separated by a frangible connection member, and wherein said first indicia and said second indicia are substantially unique to an instance of said time measuring and indication device, and wherein said first indicia and said second indicia are substantially similar such that even if said second portion is removed from said first portion said second portion is identifiable as being associated with said first portion.

27. The medical apparatus of claim 26, wherein said medical apparatus further defines an insertable medical apparatus for inserting into a patient.

28. An elapsed time measuring and indicating medical apparatus, said apparatus comprising a medical device and an actuatable and stoppable elapsed time measuring and indication device attached to said medical device, and wherein said measuring and indication device is adapted to measure and display the duration of time that said medical device is in use, and wherein if said time measuring and indication device is actuated and subsequently stopped, said time measuring and indication device indicates the amount of time that elapsed while said medical device was in use and wherein said time measuring and indication device includes a first portion having a first indicia and a second portion having a second indicia, and wherein said first portion and said second portion are separated by a frangible connection member, and wherein said first indicia and said second indicia are substantially unique to an instance of said time measuring and indication device, and wherein said first indicia and said second indicia are substantially similar such that even if said second portion is removed from said first portion said second portion is identifiable as being associated with said first portion.

* * * * *